United States Patent [19]
Sun

[11] Patent Number: 6,046,058
[45] Date of Patent: Apr. 4, 2000

[54] COLOR-CODED TEST STRIP

[76] Inventor: Ming Sun, V.P.R. Commerce Center, 1001 Lower Landing Rd., Blackwood, N.J. 08012

[21] Appl. No.: 09/197,057

[22] Filed: Nov. 20, 1998

[51] Int. Cl.[7] .................... G01N 33/558; G01N 33/543; G01N 33/53; G01N 21/00; C12M 1/00
[52] U.S. Cl. .................. 436/514; 436/514; 436/518; 436/169; 436/805; 436/810; 435/287.1; 435/287.2; 435/287.7; 435/287.9; 435/805; 435/810; 435/970; 435/973; 435/975; 422/55; 422/58; 422/61; 422/56
[58] Field of Search .................. 422/55, 58, 61, 422/56; 435/287.1, 287.2, 287.7, 287.9, 805, 810, 970, 973, 975; 436/514, 518, 169, 810, 805

[56] References Cited

U.S. PATENT DOCUMENTS

| | | | |
|---|---|---|---|
| 5,238,652 | 8/1993 | Sun et al. | 422/61 |
| 5,240,735 | 8/1993 | Lau | 427/2 |
| 5,252,496 | 10/1993 | Kang et al. | 436/529 |
| 5,260,194 | 11/1993 | Olson | 435/7.91 |
| 5,384,264 | 1/1995 | Cheng et al. | 436/525 |
| 5,500,375 | 3/1996 | Lee-Own et al. | 436/514 |
| 5,559,041 | 9/1996 | Kang et al. | 436/518 |
| 5,656,448 | 8/1997 | Kang et al. | 435/7.94 |
| 5,728,587 | 3/1998 | Kang et al. | 436/518 |

*Primary Examiner*—Rodney P. Swartz
*Assistant Examiner*—Padma Baskar
*Attorney, Agent, or Firm*—Norman E. Lehrer

[57] ABSTRACT

A test device which includes a housing having an immunochromatographic test strip therein is disclosed. The test strip is color-coded so that the presence or absence of a substance or substances in a fluid sample may be detected and identified. The strip also indicates the locations of the immunoreactions that will take place on the test strip by means of colored lines. Sample is applied onto the strip through a window and is spontaneously wicked up the test strip mobilizing a dye-microspherical antibody located in a first zone on the strip. The dye particles then move along the membrane strip by capillary action to a second zone. In the absence of specific antigen in the sample, the dye-microsphere particles attach to the antigen in the second and third zones through immunocomplexation, forming definite, visible lines. This is a negative test. In the presence of the specific antigen and/or its major metabolites in a sample, the binding of the antigen-conjugate to the antigens in the second and third zones is blocked by the sample. Thus, the immune complex formation between the antigens in the second and third zones and the dye-microsphere antibody conjugate is prevented. This is a positive test and lines will not form in the second and third zones. Multiple tests may also be performed on one test strip. The strip also contains a reference zone indicated by a visible line which is present in both positive and negative tests.

10 Claims, 2 Drawing Sheets

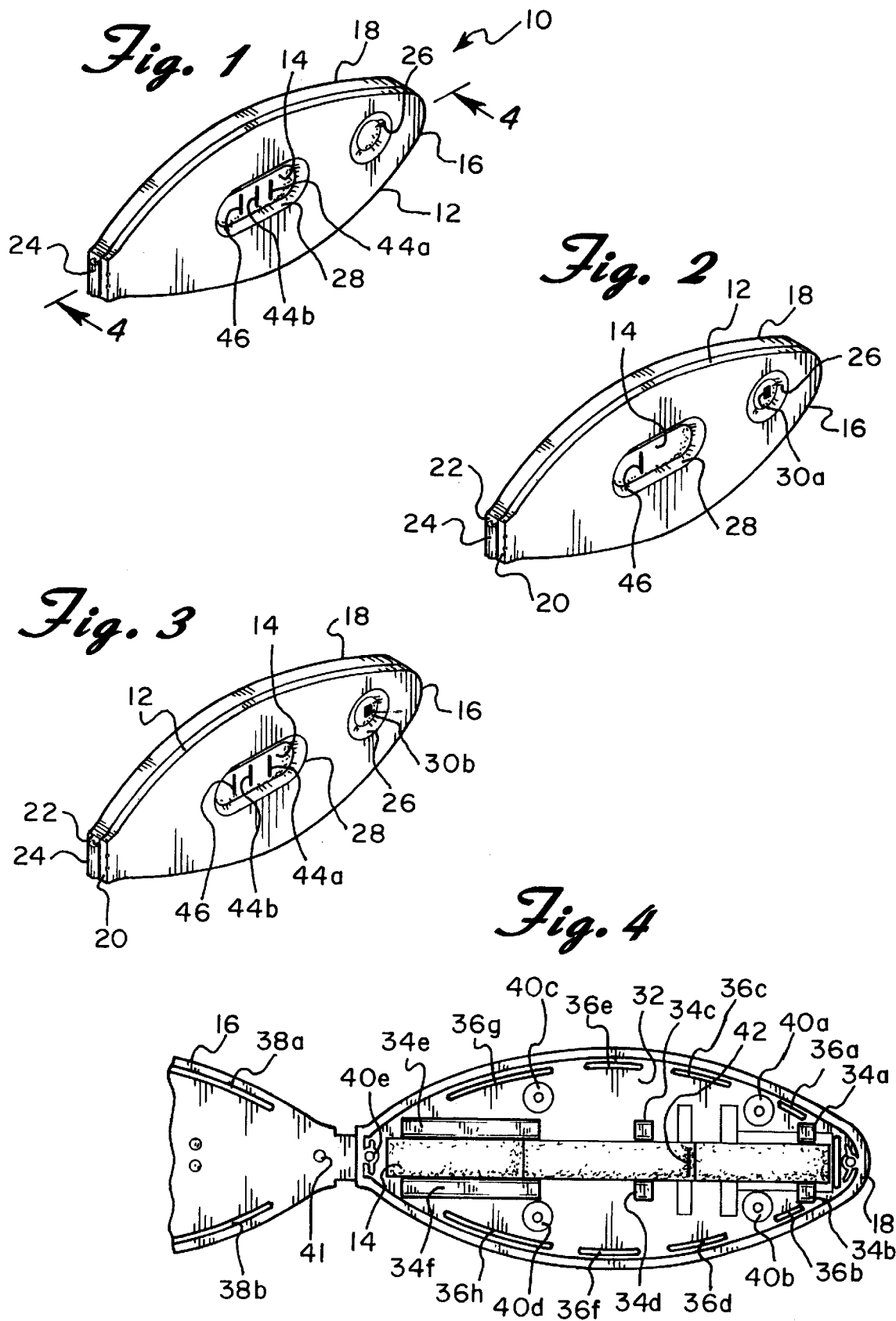

COLOR-CODED TEST STRIP

BACKGROUND OF THE INVENTION

The present invention is directed toward immunochromatographic test strips and more particularly, toward test strips that are color-coded in order to detect the presence or absence of a particular substance in a fluid sample.

The measurement of physiologically important substances in urine, serum, and tissue using immunological principles is well known. In particular, drug-specific antibodies and antigens have been used in a variety of immunological assay procedures for detecting antibodies or antigens in bodily fluids of humans and animals. Test devices are known which can identify the presence or absence of drugs of abuse, such as cocaine, opiates, and marijuana, using the protein conjugates of these drug derivatives and their accompanying antibodies.

U.S. Pat. No. 5,260,194 to Olson discloses an immunoseparating strip for determining the presence of an analyte in a test solution. The test solution contains a fluid sample, an antibody for the analyte, a conjugate of the analyte, and a label. The test device is a bibulous strip which is contacted with the test solution. The bibulous material contains a first receptor capable of binding to the conjugate of the analyte and a second receptor capable of binding to the antibody of the analyte. If the conjugate is present, a signal producing means interacts with the label and produces a signal in relation to the amount of analyte in the fluid sample. This device, however, is a complex system which requires a number of special reagents and test conditions.

U.S. Pat. No. 5,240,735 to Lau discloses a test device which includes a carrier matrix having a reactant system capable of interacting with proteins in a fluid sample to produce a visually detectable and/or measurable response based on changes in pH. The reactant system requires two dyes incorporated into the carrier matrix to provide improved color resolution and increased sensitivity to proteins. The dyes are capable of interacting with proteins and undergo a sufficient and contrasting color transition at approximately the same pH range.

U.S. Pat. No. 5,238,652 to Sun et al discloses an analytical test for assaying various drugs using immunochromatography and colored latex particles which indicate whether the fluid sample contains a particular non-protein antigen being tested. A positive result is indicated by a lack of color. This test, however, may lead to inaccurate results because the location of the reaction is unmarked, therefore, the lack of color in a positive test may be mistaken.

SUMMARY OF THE INVENTION

The present invention is designed to overcome the deficiencies of the prior art discussed above. It is an object of this invention to provide an immunochromatographic test strip which is color-coded so that the presence or absence of a substance in a fluid sample may be identified.

It is an other object of the invention to provide a test strip which indicates where the immunoreactions will take place on the strip and thereby eliminate false positive results.

It is a further object of the invention to provide a test strip which may be used to conduct more than one test.

It is a further object of the invention to provide color-coded test strips which could aid in positioning each of the test strips within a housing during production and assembly of the test devices.

In accordance with the illustrative embodiments, demonstrating features and advantages of the present invention, there is provided a test device including a housing which has an immunochromatographic test strip enclosed therein. The housing has two windows where one of the windows is used to introduce the fluid sample to the test strip and the other window is used to visualize the immunoreactions. The immunochromatographic test strip is color-coded, indicates the location of the immunoreactions, and detects and identifies the presence or absence of a substance in a fluid sample.

Other objects, features, and advantages of the invention will be readily apparent from the following detailed description of preferred embodiments thereof taken in conjugation with the drawings.

BRIEF DESCRIPTION OF THE DRAWINGS

For the purpose of illustrating the invention, there is shown in the accompanying drawings forms which are presently preferred; it being understood that the invention is not intended to be limited to the precise arrangements and instrumentalities shown.

FIG. 1 is a perspective view of the test strip and housing of the present invention;

FIG. 2 is perspective view of the test strip and housing of the present invention showing a positive test result;

FIG. 3 is a perspective view of the test strip and housing of the present invention showing a negative test result;

FIG. 4 is a cross-sectional view of the test strip housing taken along line 4—4 of FIG. 1;

DETAILED DESCRIPTION OF THE PREFERRED EMBODIMENTS

Figure 5A:
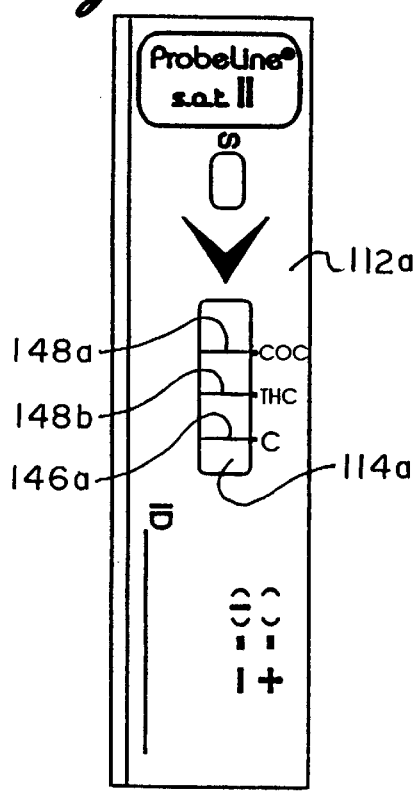
FIG. 5A illustrates a second embodiment of the present invention which includes two tests on one test strip where the strip is housed within a rectangular housing.

Referring now to the drawings in detail wherein like reference numerals have been used throughout the various figures to designate like elements, there is shown in FIG. 1 a color-coded immunochromatographic test device constructed in accordance with the principles of the present invention and designated generally as 10.

The test device 10 consists of essentially two parts: a housing 12 and a test strip 14 contained within the housing 12. The housing 12 may be made from plastic and has a top half 16 and a bottom half 18. At an end 20 of the top half 16 and corresponding end 22 of the bottom half 18, is a hinge 24 which connects the top half 16 and bottom half 18. A hinge 24 is one type of connection provided between the two halves; however, it should be realized that any connecting means well known in the art may be used. The top half 16 has at least two windows 26 and 28. Fluid sample 30a or 30b is placed on the test strip 14 through window 26 and the immunoreactions may be observed through the window 28. The test strip 14 is fit onto the inside surface 32 of the bottom half 18 of the housing 12 and is held in place by pins 34a–34f, for example, located on the inside surface 32 of the bottom half 18. Protrusions 36a–36h are located along the perimeter of the inside surface 32 of the bottom half 18 and protrusions 38a and 38b, for example, are located along the perimeter of the inside surface of the top half 16. The protrusions 36e and 36f bias protrusions 38a and 38b when the housing is closed. Holes 40a–40e are also located on the inside surface 32 of the bottom half 18 in which pins on the inside surface of the top half 16 fit in order to secure the top half 16 to the bottom half 18 of the housing. See, for example, pin 41 which fits into hole 40e in FIG. 4.

Looking at the membrane strip 14 in more detail, the test strip 14 may be a porous filter which is a pretreated membrane made of activated nylon or nitrocellulose membrane. Immunoassay reagents and components are dried on the porous membrane. The strip 14 contains preformulated reagents deposited at four reaction zones 42, 44a, 44b, and 46. The sample 30a or 30b is applied to the membrane strip 14 at one end of the strip 14. Immediately adjacent to the sample 30a or 30b is the first zone 42 which has a deposit of a defined quantity of antibody-conjugated dye or microparticles. (See FIG. 4.) The second and third zones 44a and 44b are located approximately eight to ten millimeters away from the first zone 42. The fourth zone 46 is located approximately several millimeters away from the third zone 44b. (See FIG. 1.) The second and third zones 44a and 44b, respectively, contain immobilized antigens and are the test probes for the specific antibody-antigen reactions. The fourth zone 46 is used as a reference control line for the indication of reaction completion and verification of test viability. A secondary antibody is chosen to be the reference. The reference also monitors the stability of the immunoreaction and provides an intensity ratio control, as will be more fully described below. The second zone 44a, the third zone 44b, and the fourth zone 46 are marked by colored dyes.

Colored latex particles, ranging in size from 0.1 to 0.8 micrometers are sensitized with the specific purified antibodies and are deposited in the first zone 42 on the membrane strip 14 along the flow path of the sample. The particles may be any color but the particles must be carefully blocked with protein buffer solution to prevent nonspecific aggregation. Colloidal gold is a well known alternative to latex and may be used.

The test is performed as follows: the sample 30a or 30b is applied onto the strip 14 through window 26 and is spontaneously wicked up the enclosed membrane strip 14, mobilizing the dye-microspherical antibody in the first zone 42. The dye particles then move along the membrane strip 14, by capillary action, to the second and third zones 44a and 44b, respectively. In the absence of specific antigens in the sample 30b, the dye-microsphere particles attach to the antigens in the probe zones 44a and 44b through immunocomplexation, forming definite, visible lines. (See FIG. 3.) This is a negative test.

In the presence of specific antigens and/or their major metabolites in the sample 30a, the binding of the antigen-conjugate to the antigen in the probe zones 44a and 44b is blocked by the sample 30a. Thus, the immune complex formation between the antigen in the probe zones 44a and 44b and the dye-microsphere antibody conjugate is prevented. In a positive test, lines will not form in the probe zones 44a and 44b. (See FIG. 2.)

The reference control line 46 with a different antigen or antibody reaction, as described above, is on the immunochromatographic membrane strip 14 to indicate that the test is viable and to serve as a reference control. If the test device has been properly stored and is within the expiration time limit, the control line 46 should always be present. Therefore, for all negative tests, there will be two visible lines. (See FIG. 3.) For positive tests, there will only be one visible line, i.e., the reference control line 46. (See FIG. 2.)

In a negative test, the specific antibody sensitized particles will bind to the antigens in the probe zones. When the antigen is present in the sample, the inhibition of microsphere that binds to the antigens in the probe zones will be inversely proportional to the antigen concentration in the sample. At the reference line, this is reversed. That is, the increase of the band intensity is proportional to the concentration of the antigen in the sample. In a positive test, the microspheres from the probe zones are displaced to enhance the reference line. Two reacting components could be formulated to adjust these two colored lines in response to the antigen concentration in the sample.

The immunochromatographic test is based on the analyte in the sample competing with immobilized antigens for the limited binding sites on the sensitized microparticles. At an analyte concentration above the cutoff level, there is a 100% displacement of the test band. Thus, at an equal or above the cutoff level concentration there is a complete absence of the test band. Below the cutoff level, a semi-quantitative measurement may be installed so that the microspheres displaced from the antigen conjugates could be calibrated.

The ratio of the color intensity of the reference line R to the probe line T may also be determined. This ratio (R/T) is directly proportional to the concentration of the antigen in the test sample and is a sensitive indicator of the antigen concentration in the test sample. The reference and probe lines are from the same pool of dye particles, that is, [R]+[T]=1.0. The R/T is set at approximately 0.5/0.5=1.0 for negative samples by means of probe line conjugate adjustment, i.e., two lines are at approximately equal intensities. However, when positive samples produce different levels of inhibition on the probe line, such inhibitions actually increase the available microsphere for the reference line. Thus, the increase of intensity at the reference line is at the cost of reduction of the probe line. Thus, the R/T ration is a very sensitive measure of the antigen concentration in the test sample. The R/T ratio can be calibrated against known standards.

With the present invention, a visual indication is possible as well as a measurable color change. A hand-held reflectometer, as is well known in the art, may be used to measure the intensity of the color change in the reaction zones and to quantify the test results. The advantage of using a reflectometer is that it provides an objective measure of any color change taking place during the immunoreactions whereas a visual determination is subjective and may lead to differing opinions regarding the result.

The present invention also allows for the integrity of the test to be determined. That is, before the sample is placed on the membrane strip, the reaction zones are indicated by colored lines. The zones are all the same color. Upon humidity being introduced onto the strip, the lines become blurred or smeared. In this manner, a person using the test can see that the test is defective and knows not to proceed.

The test strip may be used to detect and identify a substance within a sample, as discussed above. Furthermore, the test strip also may be used to detect and identify more than one substance within a sample. For example, two different drugs, such as cocaine and heroin, may tested on the same strip. Each probe zone, however, may have a line different in color from the other probe zones.

Alternatively, the conjugate of the analyte and the label may be bound to biotin, which system is well known in the art. The test is conducted in the manner described above, but the first zone contains an anti-biotin such as avidin or antibody for biotin. When the analyte is present, some biotinylated conjugate reaches the situs and is bound by the anti-biotin. The antibody-avidin complex is attached to the antigen-solid phase probe line through the antibody-antigen immunoreaction. The immobilized complex then bridges with biotin-microparticles by avidin-biotin coupling to form a colored band. The reference line is made of a selected secondary antibody which reacts with the biotin-microparticle conjugate independently. Signal enhancement is due to the multiple binding sites on each avidin, and the extremely high binding constant between avidin and biotin. Due to the tetravalent binding sites of avidin, more biotinylated microparticles can be bound to the probe area through a bridged complex formation, resulting in an increase of precipitin color formation of the probe line.

In a second embodiment of the present invention, as seen in FIG. 5A, the test strip 114a may be housed in a generally rectangular housing 112a. The test strip 114a has a reference line 146a and two probe zones 148a and 148b. Each probe zone detects and identifies the presence or absence of a different substance in a sample in the same manner described above. This embodiment varies from the embodiments discussed above only in the shape of the housing. Also, while the shape of the housing is shown as generally rectangular, it should be realized that this is merely exemplary and that virtually any shape may be used. Furthermore, any number of tests may be included on a single test strip, as seen, for example, in embodiments three through five illustrated in FIGS. 5B–5D.

Figure 5B:
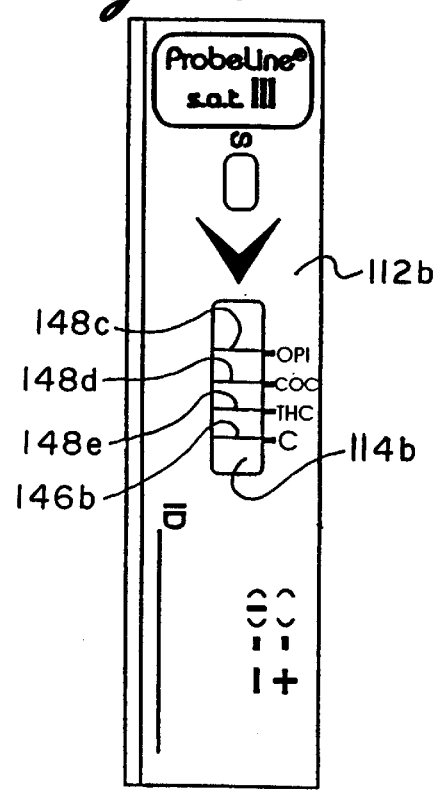
FIG. 5B illustrates a third embodiment of the present invention which includes three tests on one test strip where the strip is housed within a rectangular housing.

The third embodiment of the present invention, illustrated in FIG. 5B, is similar to the second embodiment discussed above. That is, the test strip 114b may be housed in a generally rectangular housing 112b. The test strip 114b in this embodiment, however, has a reference line 146b and three probe zones 148c, 148d, and 148e. Each probe zone, again, detects the presence or absence of a different substance in a sample in the same manner described above.

Figure 5C:
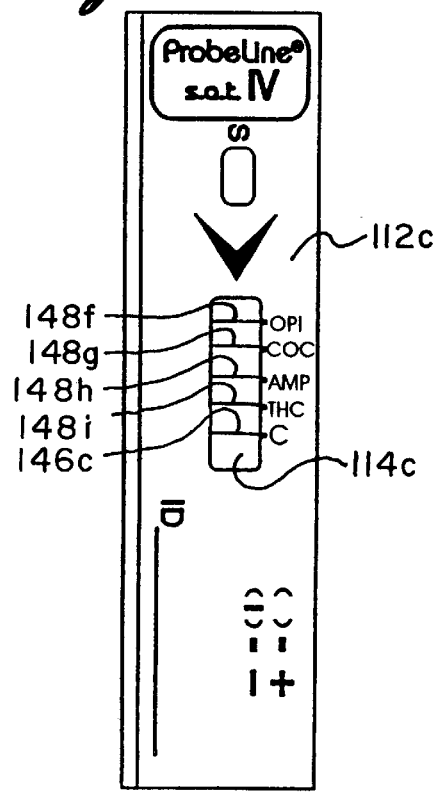
FIG. 5C illustrates a fourth embodiment of the present invention which includes four tests on one test strip where the strip is housed within a rectangular housing.

The fourth embodiment of the present invention, illustrated in FIG. 5C, is similar to the second and third embodiments discussed above. That is, the test strip 114c may be housed in a generally rectangular housing 112c. The test strip 114c in this embodiment, however, has a reference line 146c and four probe zones 148f, 148g, 148h, and 148i. Each probe zone detects and identifies the presence or absence of a different substance in a sample in the same manner described above.

Figure 5D:
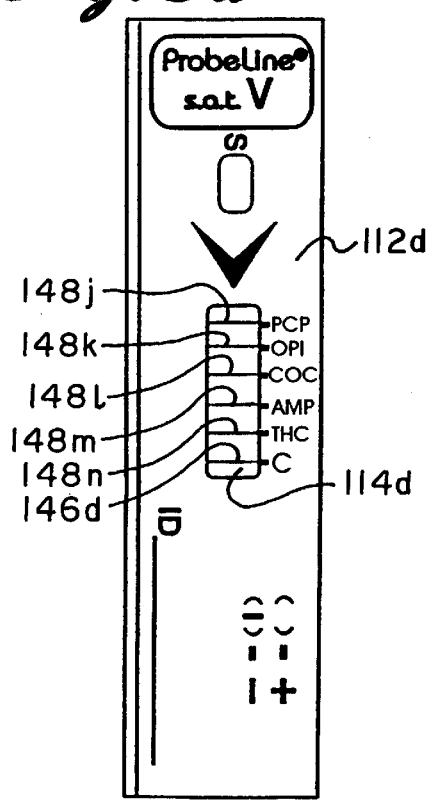
FIG. 5D illustrates a fifth embodiment of the present invention which includes five tests on one test strip where the strip is housed within a rectangular housing.

The fifth embodiment of the present invention, illustrated in FIG. 5D, is similar to the embodiments discussed above. That is, the test strip 114d may be housed in a generally rectangular housing 112d. The test strip 114d in this embodiment, however, has a reference line 146d and five probe zones 148j, 148k, 148l, 148m, and 148n. Each probe zone detects and identifies the presence or absence of a different substance in a sample in the same manner described above.

In yet another embodiment of the present invention, the test strip may be housed within a housing similar to the housing described in Applicant's co-pending application, U.S. application Ser. No. 08/953,930 which is herein incorporated by reference.

The present invention may be embodied in other specific forms without departing from the spirit or essential attributes thereof and accordingly, reference should be made to the appended claims rather than to the foregoing specification as indicating the scope of the invention.

I claim:

1. A test device comprising:

a housing and a test strip within said housing, said strip containing immunoreagents thereon and said strip having a colored reference line formed either by antigen or antibody which are immobilized on the strip for indicating the viability of the test strip prior to testing and at least one reaction zone, said at least one reaction zone having means for detecting the presence or absence of a substance in a fluid sample.

2. The test device in claim 1 wherein said detecting means is the presence or absence of a colored line located within said reaction zone.

3. The test device claimed in claim 1 wherein said housing has a top half and a bottom half.

4. The test device claimed in claim 3 wherein said top half has at least two windows therein.

5. The test device claimed in claim 3 wherein said test strip fits within said bottom half.

6. The test device claimed in claim 1 wherein said test strip contains multiple preformulated reagents.

7. The test device claimed in claim 1 further including a plurality of reaction zones wherein each of said zones includes a colored line, wherein each of said colored lines is a color different from the other of said lines.

8. The test device claimed in claim 7 wherein each of said colored lines identifies a different substance.

9. A method of performing an analytical test for detecting a substance in a fluid sample comprising the steps of:

providing a housing and a test strip within said housing, said strip containing immunoreagents thereon and said strip having a colored reference line formed either by antigen or antibody which are immobilized on the strip for indicating the viability of the test strip prior to testing and at least one reaction zone, said at least one reaction zone having means for detecting the presence or absence of a substance in a fluid sample;

placing a fluid sample on said test strip; and visually determining whether a substance is present within said fluid sample.

10. The method claimed in claim 9 wherein said step of visually determining whether a substance is present within said fluid sample includes the presence or absence of a colored line located within said reaction zone.

* * * * *